(12) United States Patent
Weber, Jr. et al.

(10) Patent No.: US 6,546,341 B2
(45) Date of Patent: Apr. 8, 2003

(54) TECHNIQUE FOR RAPID PREDICTION OF LONG-TERM HYDROPHOBIC ORGANIC CONTAMINANT DESORPTION RATES

(75) Inventors: Walter J. Weber, Jr., Ann Arbor, MI (US); Martin D. Johnson, Dunbar, WV (US)

(73) Assignee: The Regents of the University of Michigan, Ann Arbor, MI (US)

( * ) Notice: Subject to any disclaimer, the term of this patent is extended or adjusted under 35 U.S.C. 154(b) by 228 days.

(21) Appl. No.: 09/756,550

(22) Filed: Jan. 8, 2001

(65) Prior Publication Data

US 2002/0128782 A1 Sep. 12, 2002

(51) Int. Cl.$^7$ ................................................. B01D 15/00

(52) U.S. Cl. ............................. 702/32; 702/22; 702/25; 702/130; 405/128.1; 405/128.15; 210/902

(58) Field of Search ............................... 702/32, 22, 27, 702/25, 130; 405/128.1, 128.6, 130, 128.5, 264; 210/908, 902, 631, 690

(56) References Cited

U.S. PATENT DOCUMENTS 5,391,300 A * 2/1995 Webb et al. ................. 210/670

OTHER PUBLICATIONS

Brusseau, M.L.; *Environ. Sci. Technol.*, 1991, vol. 25, pp. 134–142.
Carroll, K.M.; Harkness, M.R.; Bracco, A.A.; Balcarcel, R.R.; *Environ. Sci. Technol.*, 1994, vol. 28, pp. 253–258.
Coates, J.T.; Elzerman, A.W.; *J. Contam. Hydrol.*, 1986, vol. 1, pp. 191–210.
Cornelissen, G.; van Noort, C.M.; Govers, H.A.J.; *J. Environ. Toxicol. Chem.*, 1997, vol. 16, pp. 1351–1357.
DiToro, D.M.; Horzempa, L.M.; *Environ. Sci. Technolol.*, 1982, vol. 16, pp. 594–602.
Farrell, J.; Reinhard, M.; *Environ. Sci. Technol.*, 1994, vol. 28, pp. 63–72.
Harmon, T.C.; Roberts, P.V.; *Environ. Prog.*, 1994, vol. 13, pp. 1–8.
Karickhoff, S.W.; *In Contaminants and Sediments*; Baker, R.A., Ed.; Ann Arbor Science, Ann Arbor, 1980, vol. 2, pp. 193–205.
Pavlostathls, S.G.; Mathavan, G.N.; *Environ. Sci. Technol.*, 1992, vol. 26, pp. 532–538.
Pignatello, J.J.; Frink, C.R.; Marin, P.A.; Droste, E.X.; *J. Contam. Hydrol.*, 1990, vol. 5, pp. 195–214.
Pignatello, J.J.; *Environ. Toxicol. Chem.*, 1990, vol. 9, pp. 1107–1115.
Scribner, S.L.; Benzing, T.R.; Sun, S.B.; Boyd, S.A.; *J. Environ. Qual.*, 1992, vol. 21, pp. 115–120.
pg,3
Steinberg, S.M.; Pignatello, J.J.; Sawhney, B.L.; *Environ. Sci. Technol.*, 1987, vol. 21, pp. 1201–1208.
Werth, C.J.; Reinhard, M.; *Environ. Sci. Technol.*, 1997, vol. 31, pp. 697–703.
Pignatello, J.J.; Ferrandino, F.J.; Huang, L.Q.; *Environ. Sci. Technol.*, 1993, vol. 27, pp. 1563–1571.

(List continued on next page.)

Primary Examiner—Michael Nghiem
Assistant Examiner—Hien Vo
(74) Attorney, Agent, or Firm—Brooks & Kushman P.C.

(57) ABSTRACT

A laboratory technique for rapidly predicting the long-term hydrophobic organic contaminant (HOC) desorption behavior in a contaminated soil or sediment useful for planning remediation schemes and/or assessing alternative remediation endpoint decisions employs a superheated water extraction technique for rapid prediction of long-term HOC desorption. The proposed method has great practical significance because desorption at ambient temperatures requires months or years, while high temperature experiments are accomplished in hours or days.

13 Claims, 3 Drawing Sheets

OTHER PUBLICATIONS

Connaughton, D.F.; Stedinger, J.R.; Lion, L.W.; Shuler, M.L.; *Environ. Sci. Technol.*, 1993, vol. 27, pp. 2397–2403.

Cornelissen, G.; van Zuilen, H.; van Noort, P.C.M.; *Chemosphere*, 1999, vol. 38, pp. 2369–2380.

Ten Hulscher, T.E.M.; Vrind, B.A.; Van den Heuvel, H.; Van der Velde, L.E.; Van Noort, P.C.M.; Beurskens, J.E.M.; Govers, H.A.J.; *Environ. Sci. Technol.*, 1999, vol. 33, pp. 126–132.

McGroddy, S.E.; Farrington, J.W.; *Environ. Sci. Technol.*, 1995, vol. 29, pp. 1542–1550.

White, J.C.; Kelsey, J.W. ; Hatzinger, P.B.; Alexander, M.; *Environ. Toxicol. Chem.*, 1997, vol. 16, pp. 2040–2045.

White, J.C.; Hunter, M.; Nam, K.P.; Pignatello, J.J.; Alexander, M.; *Environ. Toxicol. Chem.*, 1999, vol. 18, pp. 1720–1727.

Tang, J.X.; Carroquino, M.J.; Robertston, B.K.; Alexander, M.; *Environ. Sci. Technol.*, 1998, vol. 32, pp. 3586–3590.

Scow, K.M.; Hutson, J.; *Soil Sci. Soc. Am. J.* 1992, vol. 56, pp. 119–127.

Scow, K.M.; Hutson, J.; *Soil Sci. Soc. Am. J.* 1992, vol. 56, pp. 128–134.

Nam, K.; Alexander, M. *Environ. Sci. Technol.* 1998, vol. 32, pp. 71–74.

Lueking, A.D.; Huang, W.L.; Soderstrom–Schwarz, S.; Kim, M.S.; Weber, W.J. *J. Environ. Qual.*, 2000, vol. 29, pp. 317–323.

Allen King, R.M.; Groenevelt, H.; Warren, C.J.; Mackay, D.M.; *J. Contam. Hydrol.*, 1996, vol. 22, pp. 203–221.

Alexander, M. *Environ. Sci. Technol.* 1995, vol. 29, pp. 2713–2717.

Chung, N.H.; Alexander M. *Environ. Sci. Technol.* 1998, vol. 32, pp. 855–860.

Kan, A.T.; Fu, G.M.; Hunter, M.; Chen, W.; Ward, C.H.; Tomson, M.B. *Environ. Sci. Technol.* 1998, vol. 32, pp. 892–902.

Kelsey, J.W.; Alexander, M. *Environ. Toxicol. Chem.* 1997, vol. 16, pp. 582–585.

Hawthorne, S.B.; Yang, Y.; Miller, D.J. *Anal. Chem.* 1994, vol. 66, pp. 2912–2920.

Farrell, J.; Grassian, D.; Jones, M. *Environ. Sci. Technol.* 1999, vol. 33, pp. 1237–1243.

Grathwohl, P.; Reinhard, M. *Environ. Sci. Technol.* 1993, vol. 27, pp. 2360–2366.

Berens, A.R.; Huvard, G.S. *J. Dispersion Sci. Technol.* 1981, vol. 2, pp. 359–378.

Berens, A.R. *Polymer* 1977, vol. 18, pp. 697–704.

Nkedikizza, P.; Brusseau, M.L.; Rao, P.S.C.; Hornsby, A.G. *Environ. Sci. Technol.* 1989, vol. 23, pp. 814–820.

Arocha, M.A.; Jackson, A.P.; McCoy, B.J. *Environ. Sci. Technol.* 1996, vol. 30, pp. 1500–1507.

Ball, W.P.; Roberts, P.V. *Environ. Sci. Technol.* 1991, vol. 25, pp. 1237–1249.

Cornelissen, G.; van Noort, P.C.M.; Govers, H.A.J. *Environ. Sci. Technol.* 1998, vol. 32, pp. 3124–3131.

Wu, S.C.; Gschwend, P.M. *Environ. Sci. Technol.* 1986, vol. 20, pp. 717–725.

Pignatello, J.J.; King, B.S. *Environ. Sci. Technol.* 1996, vol. 30, pp. 1–11.

Xing, B.S.; Pignatello, J.J. *Environ. Sci. Technol.* 1997, vol. 31, pp. 792–799.

Tang, J.X.; Alexander, M. *Environ. Toxicol. Chem.* 1999, vol. 18, pp. 2711–2714.

Chung, N.; Alexander, M. *Environ. Sci. Technol.* 1999, vol. 33, pp. 3603–3606.

Hatzinger, P.B.; Alexander, M. *Environ. Sci. Technol.* 1995, vol. 29, 537–545.

Kelsey, J.W.; Kottler, B.D.; Alexaner, M. *Environ. Sci. Technol.* 1997, vol. 31, pp. 214–217.

Cornelissen, G.; Rigterink, H.; Ferdinandy, M.M.A.; Van Noort, P.C.M. *Environ. Sci. Technol.* 1998, vol. 32, pp. 966–970.

Brusseau, M.L.; Rao, P.S.C. *Environ. Sci. Technol.* 1991, vol. 25, pp. 1501–1506.

Hawthorne, S.B.; Bjorklund, E.; Bowadt, S.; Mathiasson, L. *Environ. Sci. Technol.* 1999, vol. 33, pp. 3152–3159.

Weber, W.J., Jr.; Young, T.M. *Environ. Sci. Technol.* 1997, vol. 31, pp. 1686–1691.

Young, T.M.; Weber, W.J. *Environ. Sci. Technol.* 1997, vol. 31, pp. 1686–1696.

Young, T.M.; Weber, W.J. *Environ. Sci. Technol.* 1995, vol. 29, pp. 92–97.

* cited by examiner

TECHNIQUE FOR RAPID PREDICTION OF LONG-TERM HYDROPHOBIC ORGANIC CONTAMINANT DESORPTION RATES

GOVERNMENT RIGHTS

This invention was made with government support under National Institute of Environmental Health Sciences Grant No. P42 ESO 4911, Environmental Protection Agency Grant Nos. EPA-G-R-825540. The government has certain rights in the invention.

BACKGROUND OF THE INVENTION

1. Field of the Invention

The present invention is directed to measurement of hydrophobic organic contaminants ("HOC") in soil. More particularly, the present invention is directed to a method of predicting long-term desorption rates through short term measurements.

2. Background Art

Desorption rates for the release of HOCs from soils and sediments into interstitial water are typically interpreted as biphasic [1–14], with an initial rapid desorption that takes a few hours or days followed by an extremely slow desorption that can take months or years to reach an endpoint [2, 3, 12, 13, 15], and thus may result in a significant fraction sequestered in soils or sediments[2, 9, 12, 13, 15–19]. Slow desorption can be rate-limiting for biodegradation, bioremediation, and subsurface transport [13, 20–31]. Thus, it is critical for remediation efforts and application of alternative endpoints to characterize and quantify slow desorption rates.

Several analytical methods have been proposed for predicting rapidly desorbing and bioavailable fractions of sorbed HOCs. Mild solvent extraction with butanol, propanol, methanol, or ethyl acetate for short time periods ranging from 5–10 seconds [29, 46, 47] to several minutes [29, 46, 58] often parallel trends in bioavailability measured by microbial degradation or earthworm uptake. However, the solvent, dilution, agitation, and duration of extraction needed for predictive purposes will vary with each pollutant, type of microorganism, and type of soil or sediment [21, 29, 46–50], generating an impractically large matrix and highly operational results with little predictive capability. Current developments of such a matrix from methods reported in the literature are summarized in Table 1, exemplifying the arbitrary nature of solvent extraction predictions. Furthermore, addition of organic solvents could potentially swell natural organic phases in the sediments or displace HOCs from binding sites, causing a different desorption rate control compared to extraction processes occurring in natural systems [44, 51]. Finally, these quick solvent extraction techniques do not help to predict long-term desorption rates of the resistant HOC fractions, which is the limiting factor in remediation efforts.

TABLE 1

Solvent extraction methods to rapidly predict bioavailability.

| HOC | Sorbent | % TOC | Predictive Method | Correlates to: | Ref. |
|---|---|---|---|---|---|
| Anthracene | Lima loam | 11.4 | Ethanol extraction for 1–2 minutes, then hypochlorite extraction for 2–3 minutes | Earthworm uptake, microorganism degradation, and wheat plant uptake | [46] |
| Fluoranthrenepyrene | Lima loam | 11.4 | Ethyl acetate, n-butanol, or propanol extraction for 5 seconds on a vortex mixer | Earthworm uptake, microorganism degradation, and wheat plan uptake | [46] |
| Phenanthrene | 16 soils | 0.7–11 | 71% ethanol extraction for 90 minutes | Microbial mineralization | [29] |
| Atrazine | 16 soils | 0.7–11 | 95% ethanol extraction for 10 seconds | Microbial mineralization | [29] |
| Phenanthrene | Lima loam | 8.7 | n-butanol extraction with agitation | Microbial mineralization | [49] |
| Phenanthrene | Lima loam | 8.7 | n-butanol extraction no agitation | Earthworm uptake | [49] |
| Atrazine | Lima loam | 8.7 | 9:1 methanol water extraction | Earthworm uptake | [49] |
| Atrazine | Lima loam | 8.7 | 1:1 methanol water extraction | Microbial mineralization | [49] |
| 15 PAHs, 2–6 rings | Harbor sediments | 2.3–8.2 | Desorption into water at 20 C. for 15 days with Tenax as infinite sink with agitation | Biodegradation by landforming (poor correlation) | [50] |
| Phenanthrene | Lima loam | 7.71 | 75% ethanol extraction for 5 seconds with agitation | Earthworm uptake and microbial degradation | [47] |

TABLE 1-continued

Solvent extraction methods to rapidly predict bioavailability.

| HOC | Sorbent | % TOC | Predictive Method | Correlates to: | Ref. |
|---|---|---|---|---|---|
| Pyrene | Lima loam | 7.71 | Butanol extraction for 10 seconds with agitation | Earthworm uptake and microbial degradation | [47] |
| Pheanthrene, 4-nitrophenol | Lima loam, muck, aquifer sand | 2.3–19.3 | Butanol extraction for 2 minutes with agitation | Microbial degradation | [48] |
| Phenanthrene | Peat soil, silty loam | 5.1, 43.9 | Desorption into water for 21 days with Tenax as infinite sink with agitation | Microbial mineralization earthworm uptake | [21] |

Supercritical $CO_2$ extractions have also been used to quantify the more easily desorbed HOC fractions versus ones that are more resistant to desorption [52]. This technique is attractive because the solvent density and diffusivity are easily adjusted with temperature and pressure, and the high diffusivities and low surface tensions accelerate HOC extraction. However, it has been shown that supercritical $CO_2$ desorption does not parallel aqueous desorption for phenanthrene, possibly due to swelling of amorphous organic matter matrices [53]. Also, enthalpies of phenanthrene sorption to soils and systems have significantly greater magnitudes in supercritical $CO_2$ systems than in aqueous systems, making extrapolations between the two systems inappropriate [54,55]. Furthermore, this technique does not quantitatively predict desorption rates of the more slowly desorbing, "resistant" HOC fractions.

SUMMARY OF THE INVENTION

The present invention provides a method for rapid assessment of long-term hydrophobic organic contaminant rates by measuring desorption by water at a plurality of elevated temperatures and pressures, determination of activation energies for desorption, and predicting, based on this data, long-term desorption at ordinary temperatures and pressures. The measurements are of relatively short duration as compared with the natural long-term desorption time frame.

DETAILED DESCRIPTION OF THE PREFERRED EMBODIMENT(S)

Because HOCs desorb into the aqueous phase in natural systems, it would be more preferable to conduct desorption/extraction experiments in liquid water than in non-aqueous solvents. HOC desorption from soils and sediments to an aqueous phase containing a Tenax polymeric resin with excess capacity for HOC for 15 days [50] or 21 days [21] also correlates to short-term bioavailability. Unlike non-aqueous solvent extraction systems, this method better mimics desorption in natural systems but does not characterize rates of desorption resistant fractions unless experiments are continued for impractically long time periods because slow desorption continues for months or years. This is a significant shortcoming because it is the slowly desorbing HOC fractions that often are the most difficult to remove and hamper remediation efforts.

The following procedure is effective for predicting long-term HOC desorption rapidly. Each of the five steps is discussed in more detail in the sections that follow.
(i) Measure HOC desorption rates at elevated temperatures, preferably above 50° C., and more preferably at temperatures such as 75° C., 100° C., 125° C., and 150° C.
(ii) Model high temperature desorption data with the biphasic first order desorption model to determine the rate constant for slowly desorbing HOC fraction at each temperature.
(iii) Determine apparent activation energies of the desorption process for the slowly desorbing HOC fractions through the Arrhenius relationship.
(iv) Extrapolate first order desorption rate constants to ambient temperature through the Arrhenius relationship.
(v) Adjust the time scale of high temperature desorption rate curves to predict desorption profiles at ambient temperature by the ratio of rate constants at the two temperatures.

Desorption Rate Measurements At Elevated Temperatures

Figure 1:
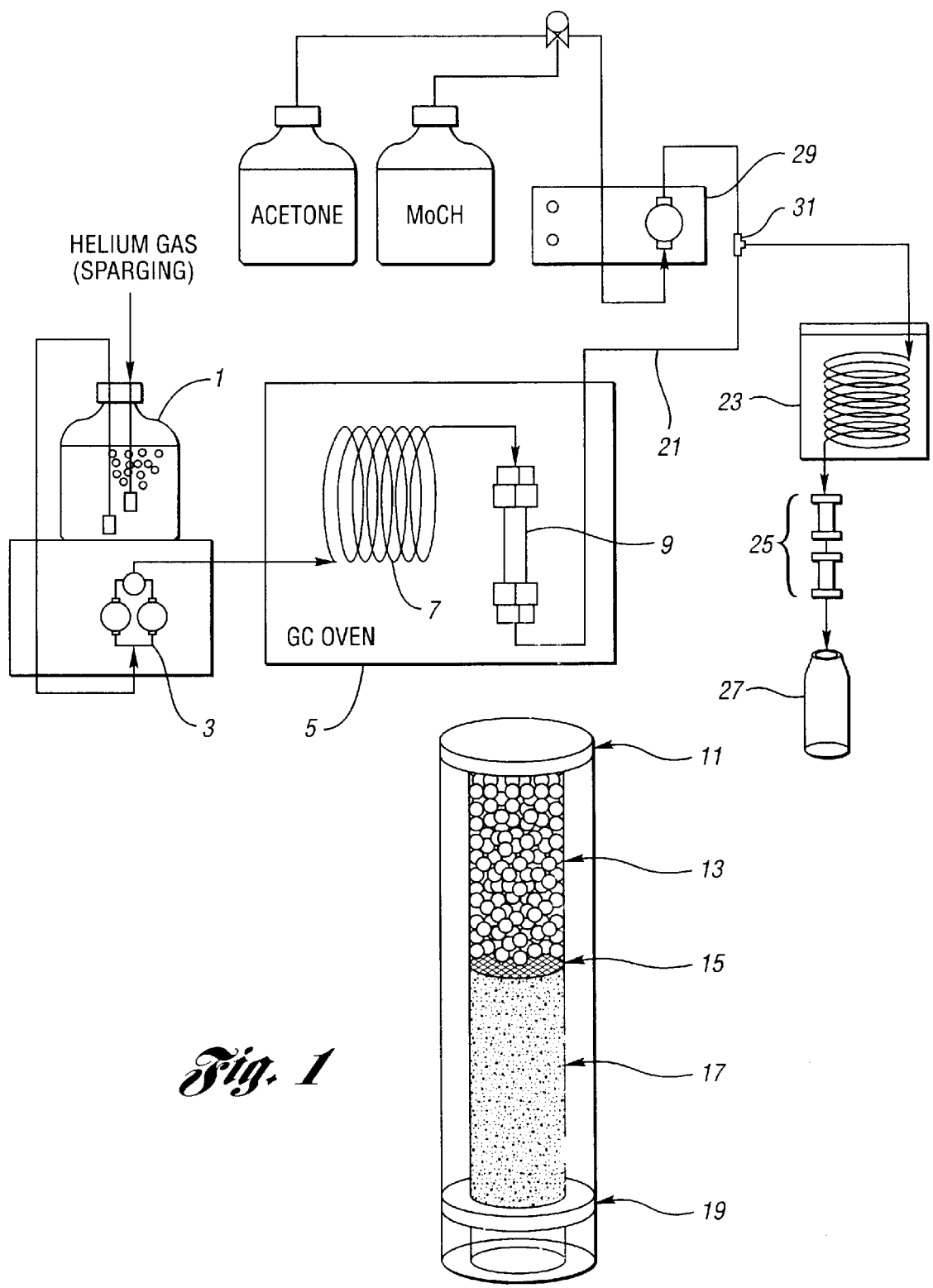
FIG. 1 is an enlarged view of one embodiment of a superheated water rapid desorption/extraction system experimental apparatus.

HOC desorption rates at high temperatures, preferably between 75 and 150° C., can be measured with a dynamic superheated water extraction system as shown in FIG. 1. The extraction system can be easily constructed, and may be performed in a manner analogous to conventional supercritical fluid extraction in a system modeled after one disclosed by Hawthorne [32]. A suitable cell may comprise a stainless steel frit filter, i.e., a 2 µm size 11 followed by stainless steel packing material 13, a stainless steel screen 15, the soil sample 17 and an additional frit 19. Other sample containers, of other materials, may be suitable as well. To summarize, distilled, deionized, helium-sparged water 1 is pumped at 1.0 ml/min by HPLC pump 3 to a GC oven 5, through a preheat coil 7, and through a stainless steel cell 9 containing the sample. The hot water containing extracted HOC exits the oven 21, passes through a cooling coil 23, and is depressurized as it flows through a series of back pressure regulators 25. All tubing is preferably 1/16 inch (1.6 mm) O.D. by 0.02 inch (0.51 mm) I.D. stainless steel. Back pressure is not required for extraction at temperatures below 100° C., but for temperatures above 100° C. enough pressure is applied to maintain water in the liquid phase. Extracted samples are collected sequentially at ambient temperature and pressure in glass vials 27. Cooling coils and back pressure regulators are flushed with methanol at a 1:2 MeOH:water volume ratio via a second HPLC pump 29 and mixing "T" 31 at the oven exit. Each desorption experiment is terminated with a 1 hour, 200–250° C., 100 atm extraction step to remove remaining HOC and close mass balances.

Desorption Rate Models

Step 2 of the above procedure suggests using a biphasic first order rate model for desorption rate data, which takes the following form:

$$\frac{q(t)}{q_0} = F_s \exp(-k_s t) + (1 - F_s)\exp(-k_r t)$$

where q(t) is solid phase HOC concentration at a given time, $q_0$ is initial solid phase sorbate concentration, $k_s$ and $k_r$ are apparent first order rate constants for slowly and rapidly desorbing fractions, respectively, $F_s$ is the slowly desorbing fraction, and $(1-F_s)$ is the rapidly desorbing fraction. Here, $k_s$ is the parameter of interest, and is observed as a function of temperature.

Alternatively, a two-parameter or three-parameter diffusion model could be used to model HOC release rates from sorbent particles. The two-parameter pore diffusion model has the following functional form, where a fraction of sorbed contaminant, $X_1$, is assumed to attain instantaneous equilibrium:

$$\frac{q(t)}{q_0} = \frac{(1-X_1)6}{\pi^2} \sum_{n=1}^{\infty} \frac{1}{n^2} \exp\left(\frac{-n^2 \pi^2 D_{s,app} t}{r^2}\right)$$

where $D_{s,app}$ is the apparent diffusion coefficient for slowly desorbing fraction and r is the particle radius. Here, $D_{s,app}/r^2$ is the parameter of interest, and is observed as a function of temperature. The three-parameter diffusion model has the functional form [35,36]:

$$\frac{q(t)}{q_0} = \frac{6}{\pi^2} \sum_{n=1}^{\infty} \frac{1}{n^2}\left[F_r \exp\left(\frac{-4n^2\pi^2 D_r t}{a_r^2}\right) + (1-F_r)\exp\left(\frac{-4n^2\pi^2 D_s t}{a_s^2}\right)\right]$$

where $F_r$ is the rapidly desorbing fraction, $D_r$ and $D_s$ are diffusion coefficients for rapidly and slowly diffusing fractions, and $a_r$ and $a_s$ are the corresponding equivalent sphere diameters. Here, $D_s/a_s^2$ is the parameter of interest, and is observed as a function of temperature. All the equations presented herein are general, and may be modified or enhanced as appropriate to include corrections for, i.e., temperature, pressure, concentration, etc.

Other rate models may also be selected. The important concept for this patented technique is to model a desorption rate parameter for the slowly desorbing fraction at different temperatures.

Basis For Activation Energy Technique

Possible rate-limiting steps responsible for slow HOC desorption from soils and sediments include intraorganic matter diffusion [1, 2, 15, 37] and hindered pore diffusion [7, 13, 14, 34, 38–41]. Diffusion through soil organic matter is analogous to diffusion in polymers, which is an activated process because diffusing molecules must penetrate through the polymeric matrix [42–44]. Pore diffusion is also an activated process and can be either sterically hindered or retarded by sorption to organic phases on pore walls. In addition, desorption from high energy sites may be an important rate limiting step. In condensed polymeric organic matter, HOCs may sorb strongly in molecular sized voids, or "holes" [44, 45], while for pore diffusion HOCs are subject to high energy sorption in molecular sized pores [6, 13, 14, 33]. Thus, slow desorption has been modeled both as a diffusion and first order desorption process. In any case, desorption rates of these activated processes can be significantly enhanced by increasing temperature, and thus it is the temperature dependence of the slowly desorbing HOC fractions on which the present invention relies. Whether modeling desorption as a first order or diffusion process, temperature dependence of the rate parameters can be described by the Arrhenius relationship.

$$k_s(T) = A\exp\left(-\frac{E_{app,d}}{RT}\right)$$

where A=Arrhenius preexponential factor, $E_{app,d}$=apparent activation energy of the desorption process, R=the universal gas constant, and T=temperature in degrees K. For diffusion.:

$$D_{s,app}(T) = D_0 \exp\left(\frac{E_{app,diff}}{RT}\right)$$

where $D_0$=Arrhenius preexponential factor and $E_{app,diff}$= apparent activation energy of diffusion.

Extrapolating Rates to Lower Temperatures

If both the activation energy for a process and the rate parameter at a given temperature are determined, the Arrhenius model can be used to calculate the rate at a different temperature:

$$\frac{k_s(T_2)}{k_s(T_1)} = \exp\left(\frac{E_{app,d}(T_2 - T_1)}{RT_1 T_2}\right)$$

where $k_s$ and $E_{app,d}$ can be replaced with $D_{s,app}$ and $E_{app,diff}$ when modeling activation energy of diffusion. For example, if $E_{app,d}$ is determined through Arrhenius modeling of experimental desorption data at different temperatures, and if $k_s$ is measured at 75° C.($T_2$), then $k_s$ at 25° C. ($T_1$) can be calculated.

Advantages Over Other Techniques

As opposed to other proposed rapid predication techniques, such as supercritical $CO_2$ extraction and organic solvent extraction, this hot water technique has the advantage of extracting with the same fluid phase, liquid water, that is operating in natural systems. Furthermore, other proposed techniques only predict rapidly desorbing HOC fractions, whereas the technique proposed here characterizes long-term slow desorption rates in a relatively short time frame. Shortcomings of other proposed techniques have been discussed previously.

Examples of Successful Application of the Method

The proposed technique was successfully applied to predict long-term, slow desorption of phenanthrene from three different geosorbents. Phenanthrene is a common HOC resulting from the petroleum and coal industry related practices. The three geosorbents, Chelsea soil, Wagner soil, and Lachine shale, vary over a wide range in their HOC sorption/desorption characteristics. Initial sorbed, solid-phase phenanthrene concentration levels were 602 µg/g, 97 µg/g, and 1080 µg/g, for Chelsea soil, Wagner soil, and Lachine shale, respectively. Phenanthrene desorption rates were highest for Chelsea soil and lowest for Lachine shale. The term "soil sample" as used herein is inclusive of geosorbent samples generally, for example of naturally occurring soils, humus, sand, shale, minerals, etc.

Figure 2:
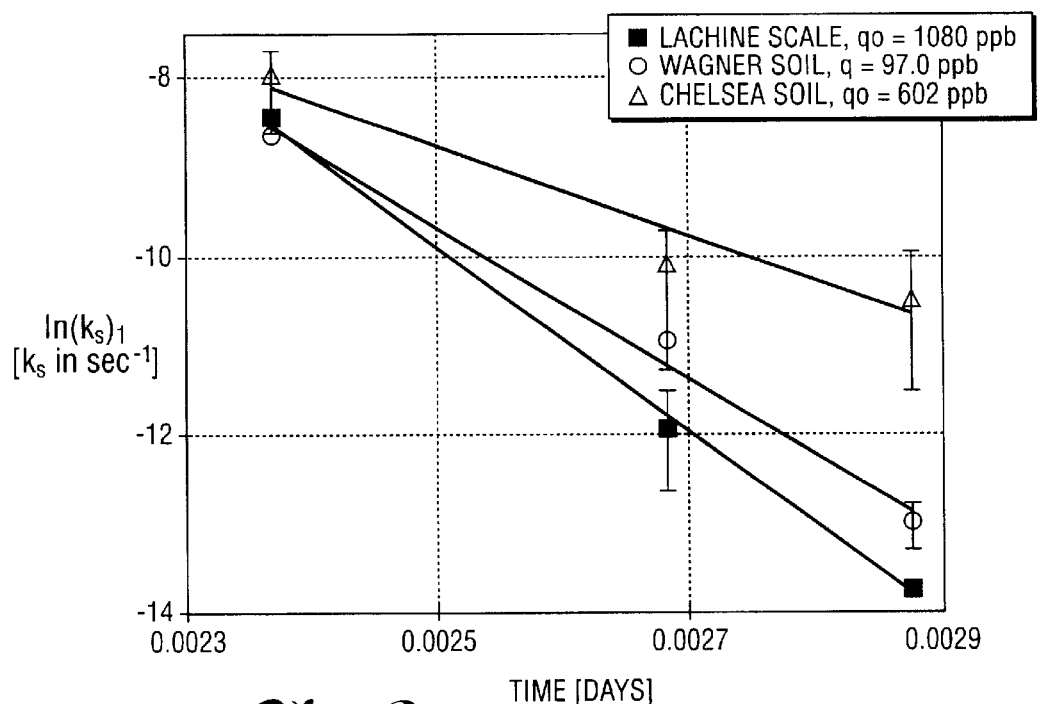
FIG. 2 illustrates Arrhenius modeling of slow first-order desorption rate constants to determine the activation energies of a desorption process.

Rates of phenanthrene desorption from each of the three contaminated sorbents were measured at 75° C., 100° C., and 150° C. using the superheated water extraction system. Next, each high temperature desorption rate curve was modeled with the biphasic first order desorption model to determine the rate constant for slowing desorbing HOC fraction, $k_s$, at each temperature. The data were modeled by the Arrhenius approach to determine apparent activation energies of the desorption process, as shown in FIG. 2. In the figure, the slopes of the lines are directly proportional to apparent activation energies of desorption. Apparent activation energies were then used to predict the ratio of phenanthrene desorption at 75° C. to desorption at 25° C. by the Arrhenius relationship. These ratio scaling factors are shown in the last column of Table 2.

Figure 3:
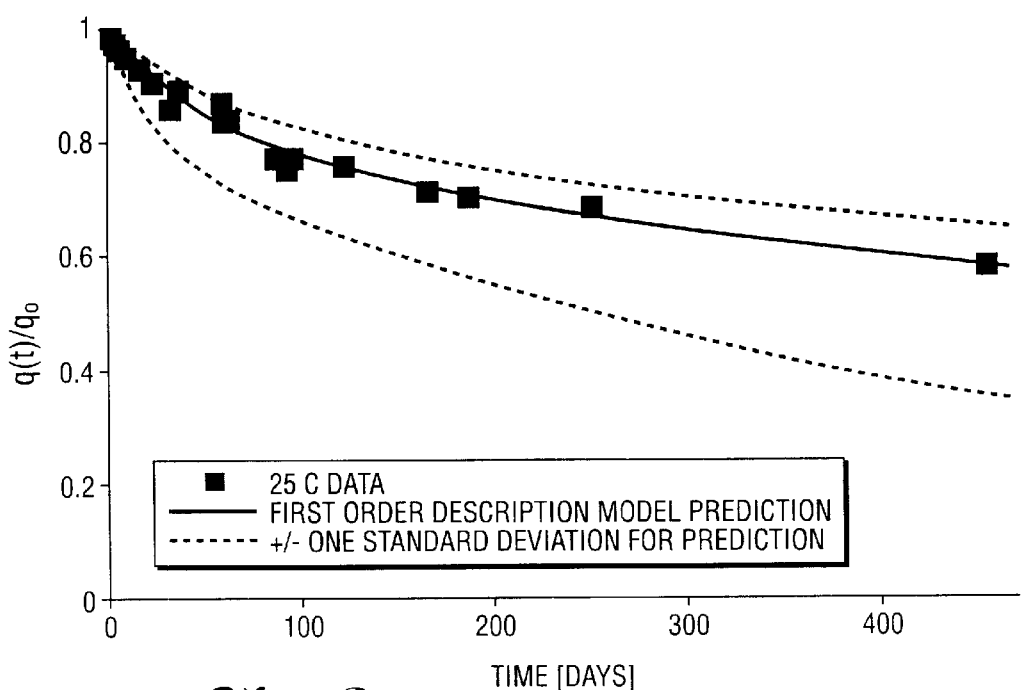
FIG. 3 illustrates the correlation of predicted long-term phenanthrene desorption rates to measured data for Lachine shale, $q_0=1080$ µg/g.
Figure 4:
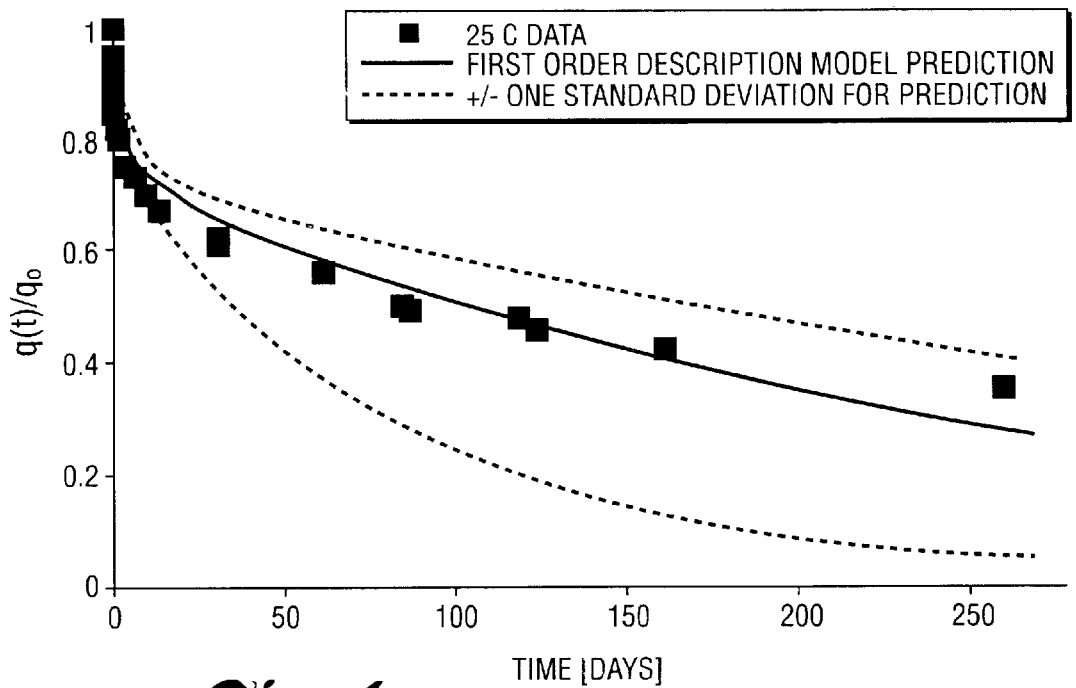
FIG. 4 illustrates the correlation of predicted long-term phenanthrene desorption rates to measured data for Wagner soil, $q_0=97$ µg/g.
Figure 5:
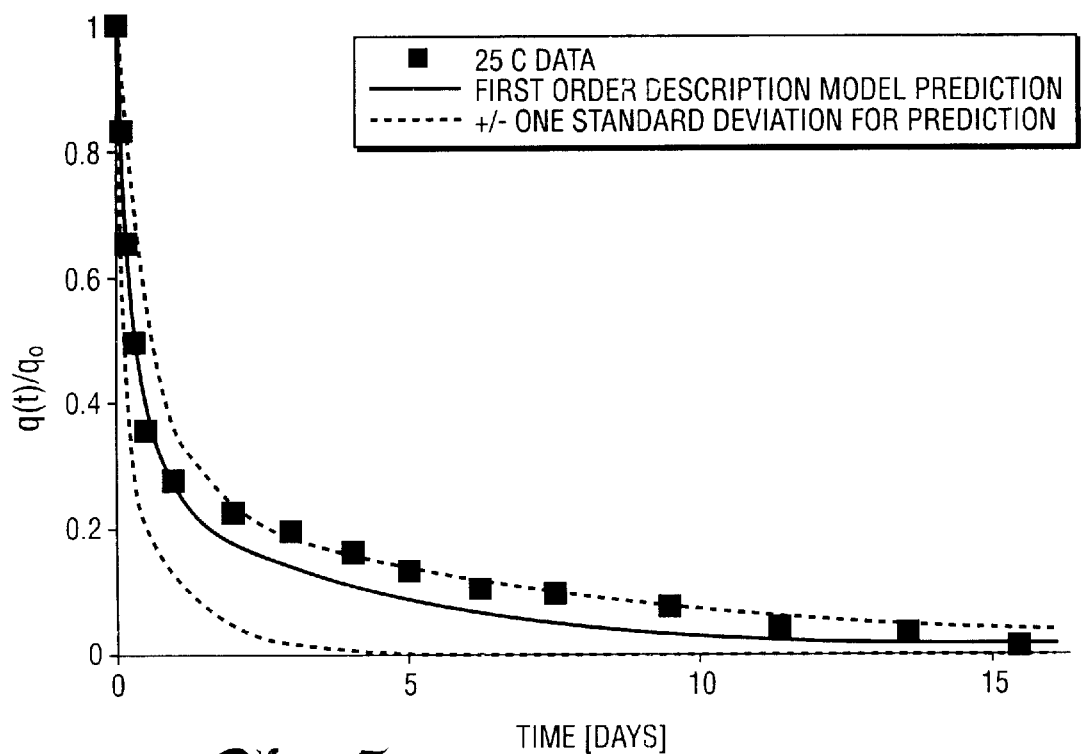
FIG. 5 illustrates the correlation of predicted long-term phenanthrene desorption rates to measured data for Chelsea soil, $q_0=602$ µg/g.

The time scale of each desorption profile at 75° C. was increased by the scaling factor from the last column in Table 2. These desorption prediction curves were compared to actual measured desorption data at 25° C. for up to 455 days, as shown in FIGS. 3 through 5. It is important to note that the prediction lines were generated completely independently from the 25° C. data points in the figures. The 25° C. desorption data points were generated by measuring phenanthrene desorption versus time in completely mixed batch reactors (CMBRs) with Tenax polymeric resin included as a high capacity sink for phenanthrene. Flame-sealed glass ampules served as CMBRs in order to minimize phenanthrene loss. This desorption measurement technique was similar to that used by Pignatello [11]. It is evident from these examples that the prediction techniques agree well with measured data even though phenanthrene desorption rates vary by orders of magnitude for the three selected samples. Thus, this is a powerful predictive technique. Desorption profiles at high temperatures matched those at 25° C., but time scales were reduced by up to three orders of magnitude. Thus, the hot water extraction technique rapidly estimates resistant fractions as well.

TABLE 2

Temperature effect on phenanthrene desorption rate.

| Sorbent | $q_o$ (µg/g) | $E_{app,d}$ (kJ/mol) | $k_s(75° C.)/k_s(25° C.)$ |
|---|---|---|---|
| Lachine shale | 1080 | 85.8 ± 9.9 | 145 |
| Wagner soil | 97.0 | 69.3 ± 18.1 | 56 |
| Chelsea soil | 602 | 41.3 ± 25.5 | 11 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

References (1) Brisseau, M. L. *Environ. Sci. Technol.* 1991, 25, 134,142.
(2) Carroll, K. M.; Harkness, M. R.; Bracco, A. A.; Balcarcel, R. R. *Environ. Sci. Technol.* 1994, 28, 253–258.
(3) Coates, J. T. *J. Contam. Hydrol.* 1986, 1, 191–210.
(4) Cornelissen, G.; van Noort, P. C. M.; Govers, H. A. J. *Environ. Toxicol. Chem.* 1997, 16, 1351–1357.
(5) Ditoro, D. M.; Horzempa, L. M. *Environ. Sci. Technol.* 1982, 16, 594–602.
(6) Farrell, J.; Reinhard, M. *Environ. Sci. Technol.* 1994, 28, 63–72.
(7) Harmon. T. C.; Roberts, P. V. *Environ. Prog.* 1994, 13, 1–8.
(8) Karickhoff, S. W. In *Contaminants and Sediments;* Baker, R. A., Ed.; Ann Arbor Science, Ann Arbor, 1980; Vol. 2, pp 193–205.
(9) Pavlostathis, S. G.; Mathavan, G. N. *Environ. Sci. Technol.* 1992, 26, 532–538.
(10) Pignatello, J. J.; Frink, C. R.; Marin, P. A. *J. Contam. Hydrol.* 1990, 5.
(11) Pignatello, J. J. *Environ. Toxicol. Chem.* 1990, 9, 1107–1115.
(12) Scribner, S. L.; Benzing, T. R.; Sun, S. B.; Boyd, S. A. *J. Environ. Qual.* 1992, 21, 115–120.
(13) Steinberg, S. M.; Pignatello, J. J.; Sawhney, B. L. *Environ. Sci. Technol.* 1987, 21, 1201–1208.
(14) Werth, C. J.; Reinhard, M. *Environ. Sci. Technol.* 1997, 31, 697–703.
(15) Pignatello, J. J.; Ferrandino, F. J.; Huang, L. Q. *Environ. Sci. Technol.* 1993, 27, 1563–1571.
(16) Connaughton, D. F.; Stedinger, J. R.; Lion, L. W.; Shuler, M. L. *Environ. Sci. Technol.* 1993, 27, 2397–2403.
(17) Cornelissen, G.; van Zuilen, H.;van Noort, P. C. M. *Chemosphere* 1999, 38, 2369–2380.
(18) Ten Hulscher, T. E. M.; Vrind, B. A.; Van den Heuvel, H.; Van der Velde, L. E.; Van Noort, P. C. M.; Beurskens, J. E. M.; Govers, H. A. J. *Environ. Sci. Technol.* 1999, 33, 126–132.
(19) McGroddy, S. E. Farrington, J. W. *Environ. Sci. Technol.* 1995, 29, 1542–1550.
(20) White, J. C.; Kelsey, J. W.; Hatzinger, P. B.; Alexander, M. *Environ. Toxicol. Chem.* 1997, 16, 2040–2045.
(21) White, J. C.; Hunter, M.; Nam, K. P.; Pignatello, J. J.; Alexaner, M. *Environ. Toxicol. Chem.* 1999, 18, 1720–1727.
(22) Tang, J. X.; Carroquino, M. J.; Robertson, B. K.; Alexander, M. *Environ. sci. Technol.* 1998, 32, 3586–3590.
(23) Scow, K. M.; Hutson, J. *Soil Sci. Soc. Am. J.* 1992, 56, 119–127.
(24) Scow, K. M.; Hutson, J. *Soil Sci. Soc. Am. J.* 1992, 56, 128–134.
(25) Nam, K.; Alexander, M. *Environ. Sci. Technol.* 1998, 32, 71–74.
(26) Lueking, A. D.; Huang, W. L.; Soderstrom-Schwarz, S.; Kim, M. S.; Weber, W. J. *J. Environ. Qual.* 2000, 29, 317–323.
(27) Allen King, R. M.; Groenevelt, H.; Warren, C. J.; Mackay, D. M. *J. Contam. Hydrol.* 1996, 22, 203–221.
(28) Alexander, M. *Eniviron. Sci. Technol.* 1995, 29, 2713–2717.
(29) Chung, N. H.; Alexander M. *Environ. Sci. Technol.* 1998, 32, 855–860.
(30) Kan, A. T.; Fu, G. M.; Hunter, M.; Chen, W.; Ward, C. H.; Tomson, M. B. *Environ. Sci. Technol.* 1998, 32, 892–902.
(31) Kelsey, J. W.; Alexander, M. *Environ. Toxicol. Chem.* 1997, 16, 582–585.
(32) Hawthorne, S. B.; Yang, Y.; Miller, D. J. *Anal. Chem.* 1994, 66, 2912–2920.
(33) Farrell, J.; Grassian, D.; Jones, M. *Environ. Sci. Technol.* 1999, 33, 1237–1243.

(34) Grathwohl, P.; Reinhard, M. *Environ. Sci. Technol.* 1993, 27, 2360–2366.
(35) Berens, A. R.; Huvard, G. S. *J. Dispersion Sci. Technol.* 1981, 2, 359–378.
(36) Berens, A. R. *Polymer* 1977, 18, 697–704.
(37) Nkedikizza, P.; Brusseau, M. L.; Rao, P. S. C.; Hornsby, A. G. *Environ. Sci. Technol.* 1989, 23, 814–820.
(38) Arocha, M. A.; Jackson, A. P.; McCoy, B. J. *Environ. Sci. Technol.* 1996, 30, 1500–1507.
(39) Ball, W. P.; Roberts, P. V. *Environ. Sci. Technol.* 1991, 25, 1237–1249.
(40) Cornelissen, G.; van Noort, P. C. M.; Govers, H. A. J. *Environ. Sci. Technol.* 1998, 32, 3124–3131.
(41) Wu, S. C.; Gschwend, P. M. *Environ. Sci. Technol.* 1986, 20, 717–725.
(42) Veith, W. R. *Diffusion in and Through Polymers: Principles and Applications;* Oxford University Press: New York, 1991.
(43) Rogers, C. E. *The phusics and chemistry of the organic solid state;* Interscience Publishers; New York, 1965; Vol. 2.
(44) Pignatello, J. J.; Xing, B. S. *Environ. Sci. Technol.* 1996, 30, 1–11.
(45) Xing, B. S.; Pignatello, J. J. *Environ. Sci. Technol.* 1997, 31, 792–799.
(46) Tang, J. X.; Alexander, M. *Environ. Toxicol. Chem.* 1999, 18, 2711–2714.
(47) Chung, N.; Alexander, M. *Environ. Sci. Technol.* 1999, 33, 3603–3606.
(48) Hatzinger, P. B.; Alexander, M. *Environ. Sci. Technol.* 1995, 29, 537–545.
(49) Kelsey, J. W.; Kottler, B. D.; Alexaner, M. *Environ. Sci. Technol.* 1997, 31, 214–217.
(50) Cornelissen, G.; Rigterink, H.; Ferdinandy, M. M. A.; Van Noort, P. C. M. *Environ. Sci. Technol.* 1998, 32, 966–970.
(51) Brusseau, M. L.; rao, P. S. C. *Environ. Sci. Technol.* 1991, 25, 1501–1506.
(52) Hawthorne, S. B.; Bjorklund, E.; Bowadt, S.; Mathiasson, L. *Environ. Sci. Technol.* 1999, 33, 3152–3159.
(53) Weber, W. J., Jr.; Young, T. M. *Environ. Sci. Technol.* 1997, 31, 1686–1691.
(54) Young, T. M.; Weber, W. J. *Environ. Sci. Technol.* 1997, 31, 1686–1696.
(55) Young, T. M.; Weber, W. J. *Environ. Sci. Technol.* 1995, 29, 92–97.

What is claimed is:

1. A method for measuring desorption rates of hydrophobic organic contaminate (HOC) in soil samples, said method comprising:
   a) extracting a soil sample with liquid water at at least two different temperatures, each greater than ambient temperature;
   b) determining hydrophobic organic contaminant desorption rate constants at at least two different temperatures, said temperatures being the temperatures at which said soil sample is extracted;
   c) determining the apparent activation energy of desorption of hydrophobic organic contaminant from the respective rate constants at said at least two different temperatures of step b);
   d) extrapolating said first order desorption rate constant to ambient temperature; and
   e) adjusting the time scale of a higher temperature desorption rate curve to ambient temperature time scale by the ratio of the rate constants at said higher temperature to ambient temperature to predict the ambient temperature desorption profile.

2. The method of claim 1 wherein a lowest temperature extraction takes place at a temperature above about 50° C.

3. The method of claim 1 wherein a lowest temperature extraction takes place at a temperature above about 75° C.

4. The method of claim 1 wherein at least one extraction temperature is greater than 100° C.

5. The method of claim 1, wherein said apparent activation energies are calculated using the Arrhenius relationship.

6. The method of claim 1, wherein extrapolation of desorption rate constants to ambient temperature is made with use of the Arrhenius relationship.

7. The method of claim 1, wherein ambient temperature is below 35° C.

8. The method of claim 1, wherein ambient temperature is 25° C.

9. The method of claim 1, wherein said step of determining said desorption rate constant employs a biphasic first order rate model.

10. The method of claim 9, wherein said biphasic first order rate model takes the form $$\frac{q(t)}{q_0} = F_s \exp(-k_s t) + (1 - F_s)\exp(-k_r t)$$

where q(t) is solid phase HOC concentration at a given time, $q_0$ is initial solid phase sorbate concentration, $k_s$ and $k_r$ are apparent first order rate constants for slowly and rapidly desorbing fractions, respectively, $F_s$ is the slowly desorbing fraction, and $(1-F_s)$ is the rapidly desorbing fraction.

11. The method of claim 1, wherein said step of determining said desorption rate constant employs a two-or three-parameter diffusion model.

12. The method of claim 11, wherein a two-parameter model is used, having the following form where a fraction of sorbed contaminant, $X_1$, is assumed to attain instantaneous equilibrium:

$$\frac{q(t)}{q_0} = \frac{(1-X_1)6}{\pi^2} \sum_{n=1}^{\infty} \frac{1}{n^2} \exp\left(\frac{-n^2\pi^2 D_{s,app} t}{r^2}\right)$$

where $D_{s,app}$ is the apparent diffusion coefficient for slowly desorbing fraction and r is the particle radius.

13. The method of claim 11, wherein a three-parameter diffusion model is employing, having the form $$\frac{q(t)}{q_0} = \frac{6}{\pi^2} \sum_{n=1}^{\infty} \frac{1}{n^2}\left[F_r \exp\left(\frac{-4n^2\pi^2 D_r t}{a_r^2}\right) + (1-F_r)\exp\left(\frac{-4n^2\pi^2 D_s t}{a_s^2}\right)\right]$$

where $F_r$ is the rapidly desorbing fraction, $D_r$ and $D_s$ are diffusion coefficients for rapidly and slowly diff-using fractions, and $a_r$ and $a_s$ are the corresponding equivalent sphere diameters.

* * * * *